US00PP35218P2

(12) United States Plant Patent
Chaussard

(10) Patent No.: US PP35,218 P2
(45) Date of Patent: Jun. 13, 2023

(54) ABELIA PLANT NAMED 'MINABCRIS01'

(50) Latin Name: ***Abelia* x *grandiflora***
Varietal Denomination: Minabcris01

(71) Applicant: Hortival Diffusion SAS, Beaufort en Valee (FR)

(72) Inventor: Pierre Chaussard, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 0 days.

(21) Appl. No.: 18/077,454

(22) Filed: Dec. 8, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Abelia* plant named 'Minabcris01' is disclosed, characterized by large, abundant, pendulous white flowers, and green foliage with red edges. Plants have vigorous, rounded habits. The new variety is an *Abelia*, normally produced as an outdoor garden or container plant.

3 Drawing Sheets

Latin name of the genus and species: *Abelia* x *grandiflora*.
Variety denomination: 'MINABCRIS01'.

BACKGROUND OF THE INVENTION

The new *Abelia* cultivar is a product of a planned breeding program by the inventor to develop new *Abelia* with large white flowers. The seed parent is an unpatented, internal *Abelia* x *grandiflora* seedling #11623. The pollen parent is the unpatented variety *Abelia* x *grandiflora* 'Sherwood'. The crossing resulting in the new variety was made at a nursery in La Menitre, France in September 2010.

The new cultivar was found and selected as an interesting new variety in September 2012, at the same nursery in La Menitre, France.

Asexual reproduction of the new cultivar 'Minabcris01' was first performed in September 2012 in La Menitre, France, by softwood cuttings. Subsequent propagation has shown that the unique features of this cultivar are stable and reproduced true to type in successive generations. Date of first sale is Mar. 1, 2022, in the France. This sale was made directly by the inventor or one who obtained the claimed invention directly or indirectly from the inventor. This sale and all public disclosures made between Mar. 1, 2022, and the filing of this application fall within the exception allowed under 102(b)(1).

SUMMARY OF THE INVENTION

The cultivar 'Minabcris01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Minabcris01'. These characteristics in combination distinguish 'Minabcris01' as a new and distinct *Abelia* cultivar:

1. Large, pendulous white flowers.
2. Rounded growth habit.
3. Heavy flowering.

PARENT COMPARISON

Plants of the new cultivar 'Minabcris01' are similar to plants of the seed parent variety in most horticultural characteristics, however, plants of the new cultivar 'Minabcris01' differ in the following:

1. Flower size of the new variety is slightly smaller than flower size of the seed parent.
2. Flower color of the new variety is white, while the flower color of the seed parent is lavender.
3. Leaves of the new variety are longer than leaves of the seed parent.
4. Leaf color of the new variety is green with a red edge, while leaf color of the seed parent is darker green.

Plants of the new cultivar 'Minabcris01' are similar to plants of the pollen parent variety in most horticultural characteristics, however, plants of the new cultivar 'Minabcris01' differ in the following:

1. Flower size of the new variety is larger than flower size of the pollen parent.
2. Flowers of the new variety are hanging, while flowers of the pollen parent are erect.
3. Stamen color of the new variety is white, while stamen color of the seed parent is lavender.
4. Growth habit of the new variety is rounded, while growth habit of the pollen parent is more vigorous.
5. Leaves of the new variety are matte, while leaves of the pollen parent are glossy.

COMMERCIAL COMPARISON

Plants of the new cultivar 'Minabcris01' can be compared to the variety *Abelia* 'Mincautri' U.S. Plant Pat. No. 33,457.

These varieties are similar in most horticultural characteristics however, 'Minabcris01' differs in the following:

1. The new variety has pendulous flowers; this comparator has outwardly facing flowers.
2. The new variety has solid colored foliage; this comparator has variegated foliate.

BRIEF DESCRIPTION OF THE PHOTOGRAPHS

The accompanying photograph in FIG. 1 illustrates in full color a plant of 'Minabcris01' during the summer grown outdoors, at approximately 1.5 years old.

Figure 1:
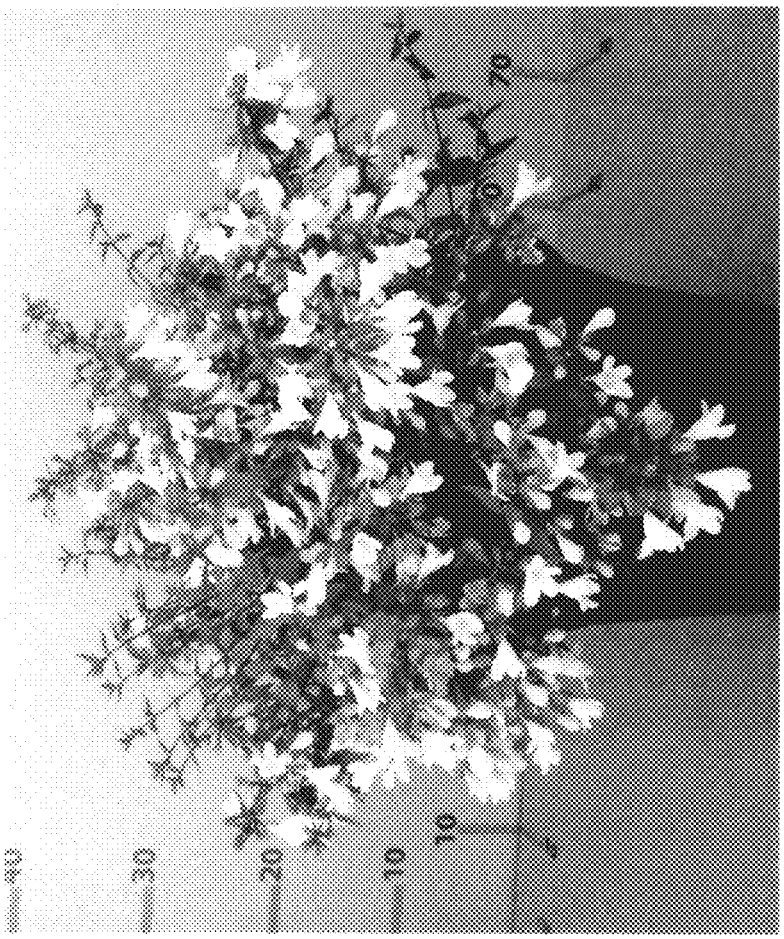
Figure 2:
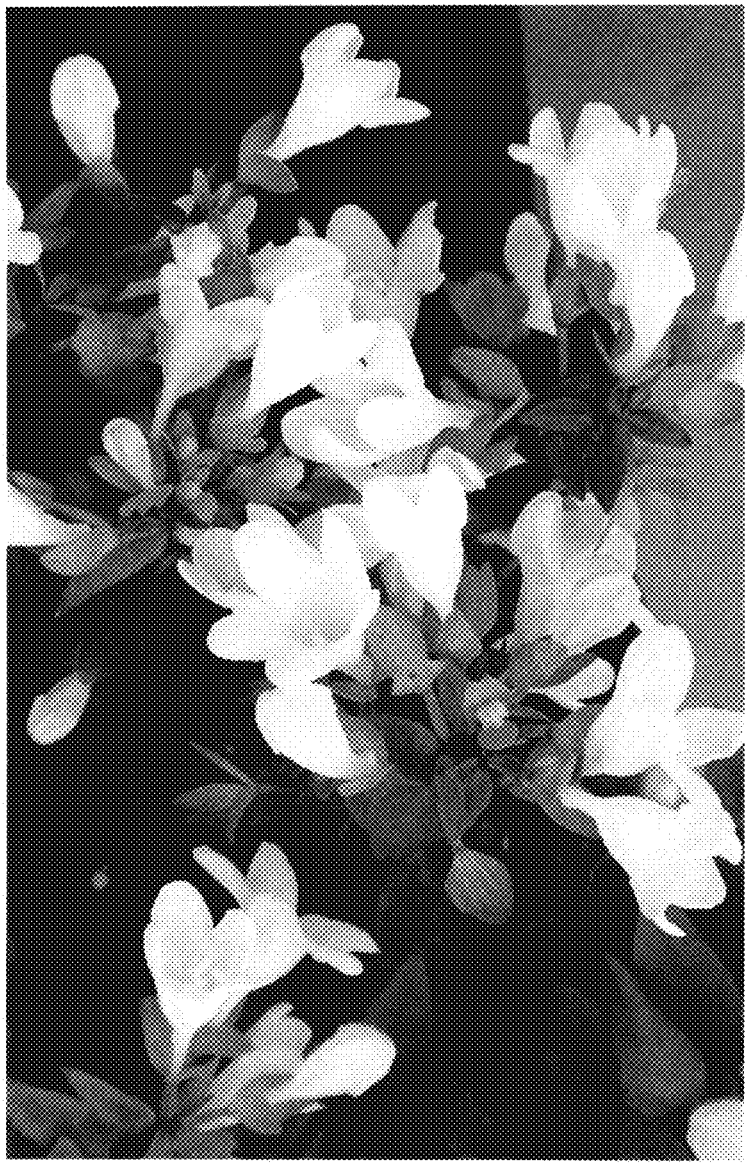
FIG. 2 illustrates a close-up view of typical flowers of 'Minabcris01'.
Figure 3:
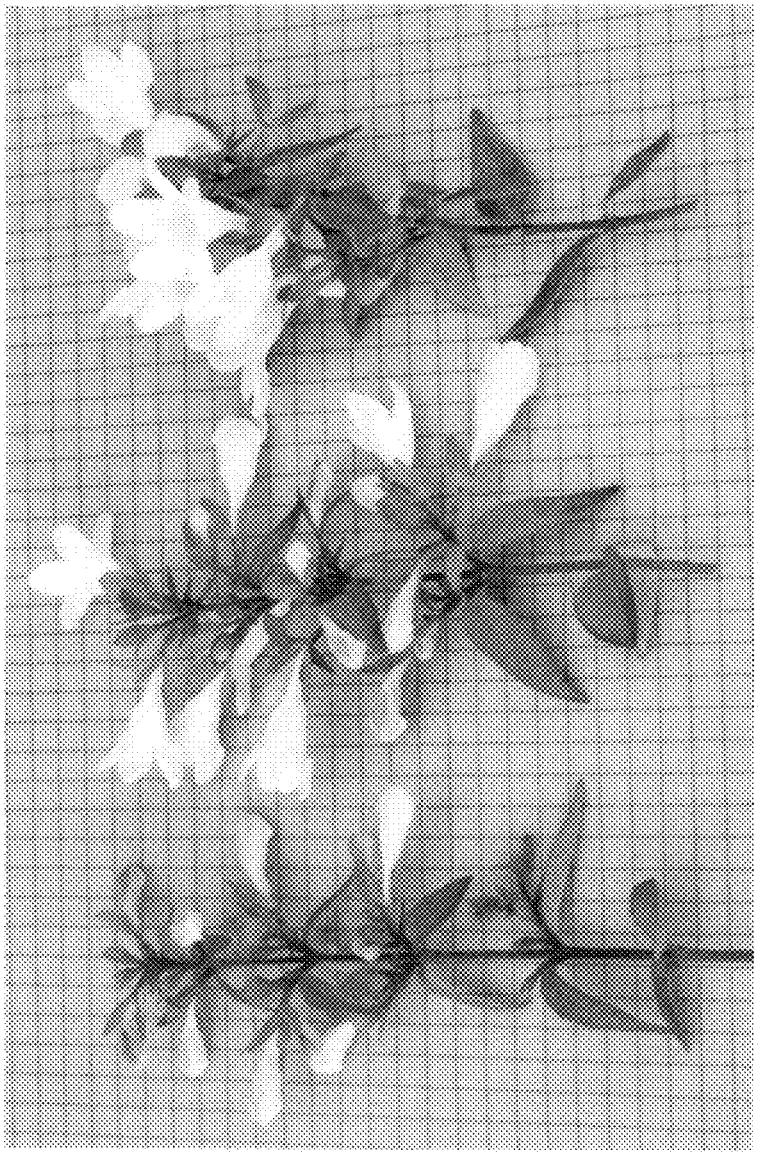
FIG. 3 illustrates flowering stem coloration at 3 different stages. The stem on the far right is the youngest, the stem in the center is nearly mature and the stem on the far right in the image is the most mature.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'Minabcris01' plants grown in a polygreenhouse in Grand Haven, Mich. Measurements were taken during September 2022. The plants were about 2 to 3 years old in 3-gallon containers. The growing temperature ranged from approximately 18° C. to 27° C. during the day and 5° C. to 10° C. at night. Measurements and numerical values represent averages of typical plant types.

Botanical classification: *Abelia* x *grandiflora* 'Minabcris01'.

PROPAGATION

Time to initiate roots: 1 to 2 months at approximately 18° C. to 27° C. in the summer.

Time to produce a rooted young plant: About 40 days at approximately 18° C. to 27° C.

Root description: Moderately dense, freely branching, thin, fibrous, and fleshy. White to tan in color, not accurately measured by the color chart.

PLANT

Plant type: Perennial flowering shrub.
Age of plant described: 2 to 3 years old.
Growth habit: Upwards and outwards.
Pot size of plant described: 3-gallon pot.
Overall plant shape: Rounded, mounded.
Height: 35 cm.
Plant spread: 60 cm.
Plant vigor: Quite vigorous.
Growth rate: Moderate.
Branching characteristics: Basal branching, some pinching required to encourage a rounded habit.
Length of primary lateral branches: 45 cm.
Diameter of lateral branches:
- *Main branch.*—7 mm.
- *Branchlets.*—2 mm.

Quantity of lateral branches: 5 to 10 main basal branches with 5 to 10 branches emerging from each.

Stem:
- *Stem shape.*—Rounded.
- *Stem strength.*—New Growth: Durable and somewhat flexible. Old Growth: Strong.
- *Color.*—New Growth: Upper Surface: RHS Greyed-Red 181A. Under Surface: RHS Green 139D. Old Growth: Near RHS Grey-Brown 199D.
- *Pubescence.*—None.
- *Angle of attachment.*—45 to 60° from parallel.

Internode length: Average 3 cm.

FOLIAGE

Leaf:
- *Arrangement.*—Opposite.
- *Leaf shape.*—Lanceolate.
- *Average length.*—3 cm.
- *Average width.*—1 cm.
- *Apex.*—Acute/acuminate.
- *Base.*—Oblique.
- *Margin.*—Entire.
- *Texture of top surface.*—Glossy, but textured with fine coarse hairs.
- *Texture of bottom surface.*—Lightly pubescent along midline only, otherwise glabrous.
- *Color.*—Young Foliage Upper Side: RHS Greyed-Orange 175A to Greyed-Red 178B. Young Foliage Under Side: RHS Greyed-Orange 174B with Yellow-Green 146C. Mature Foliage Upper Side: RHS Green 137A. Mature Foliage Under Side: RHS Yellow-Green 146C.
- *Venation.*—Pattern: Pinnate. Color Upper Side: RHS Yellow-Green 146C. Color Under Side: RHS Yellow-Green 146C.
- *Petiole.*—Average Length: 1.5 mm. Diameter: 1 mm. Petiole Color Upper Side: RHS Yellow-Green 146C, with Greyed-Red 178B along margin. Petiole Color Lower Side: RHS Yellow-Green 146C. Petiole Texture: Slightly pubescent abaxially.

FLOWER

Natural flowering season: June through September.

Flower arrangement: Terminally flowering with groups of 2-4 (commonly 4) salverform flowers emerging from axillary leaf nodes. Pendulous flowers.

Flower form: Salverform.

Quantity of flowers per lateral stem: About 10 per branchlet.

Quantity of buds per lateral stem: About 10 per branchlet.

Quantity of flowers and buds per plant: Several hundred on average.

Flower:
- *Depth.*—2 cm.
- *Diameter.*—2 cm.
- *Shape.*—Single whorl with 5 recurved petals.
- *Aspect.*—Outwards.
- *Throat diameter.*—7 mm.
- *Flower tube length.*—1.5 cm.
- *Flower tube diameter.*—2 mm.
- *Persistence.*—Self-cleaning.
- *Fragrance.*—Mild, moderately sweet and perfumy.

Bud:
- *Shape.*—Spatulate.
- *Length.*—1.25 cm.

*Diameter.*—5 mm.
*Color.*—RHS Yellow-Green 150D.

Petal:
*Appearance.*—Smooth and soft.
*Arrangement.*—Stellate.
*Number.*—5.
*Petal shape.*—Elliptic to oblong.
*Margin.*—Entire.
*Tip shape.*—Obtuse.
*Length from throat.*—7.5 mm.
*Width.*—5 mm.
*Texture.*—Upper: Glabrous and silky. Lower: Glabrous and silky.
*Throat texture.*—Glabrous, silky.
*Tube texture.*—Glabrous, silky.
*Color.*—When Opening: Inner Surface: RHS White NN155B. Outer Surface: RHS White NN155B. Fully Opened: Upper Surface: RHS White NN155B. Lower Surface: RHS White NN155B. Flower Tube Color: RHS White NN155B. Flower Throat Color: RHS White NN155B. Vein Color: Upper Surface: RHS White NN155B. Lower Surface: RHS White NN155B. Vein Color, Tube: RHS White NN155B.

Sepal:
*Arrangement.*—Whorl.
*Number.*—2 to 3.
*Shape.*—Elliptic to lanceolate.
*Tip.*—Acute, sometimes notched.
*Base.*—Attenuate.
*Margin.*—Entire.
*Length.*—1 cm.
*Width.*—4 mm.
*Texture, upper.*—Glabrous.
*Texture, lower.*—Glabrous.
*Color.*—Upper Surface: RHS Green 137A, tinted Greyed-Orange 174B-C, becoming Greyed-Red 176B to 178B after flower is shed. Lower Surface: RHS Green 137A, tinted Greyed-Orange 174B-C, becoming Greyed-Red 176B to 178B after flower is shed.
*Calyx shape.*—Collar-like.

Peduncle:
*Length.*—5 mm.
*Diameter.*—2 mm.
*Color.*—RHS Green 137A, tinted Greyed-Orange 174B-C, becoming Greyed-Red 176B to 178B after flower is shed.
*Orientation.*—45°.
*Strength.*—Good.
*Texture.*—Very slightly pubescent.

Pedicel: None.

REPRODUCTIVE ORGANS

Stamens:
*Number.*—4.
*Filament length.*—1 cm.
*Filament color.*—RHS White 155B.

Anthers:
*Shape.*—Linear.
*Length.*—2 mm.
*Color.*—RHS Greyed-Yellow 162D.
*Pollen color.*—RHS Greyed-Yellow 162D.
*Pollen amount.*—Sparse to moderate.

Pistil:
*Number.*—1.
*Length.*—1 cm.
*Style.*—Length: 9 mm. Color: RHS White 155B.
*Stigma.*—Shape: Rounded/globose. Color: RHS White 155B.

OTHER CHARACTERISTICS

Seeds and fruits: Not observed.

Disease/pest resistance: Neither resistance nor susceptibility to normal diseases and pests of *Abelia grandiflora* have been observed.

Temperature tolerance: Tolerant from −31° C. to 38° C.

What is claimed is:

1. A new and distinct cultivar of *Abelia* plant named 'Minabcris01' as herein illustrated and described.

* * * * *